United States Patent [19]

Chen et al.

[11] Patent Number: 5,248,796
[45] Date of Patent: Sep. 28, 1993

[54] TAXOL DERIVATIVES

[75] Inventors: Shu-Hui Chen, New Haven; Vittorio Farina, West Hartford, both of Conn.

[73] Assignee: Bristol-Myers Squibb Company, New York, N.Y.

[21] Appl. No.: 900,365

[22] Filed: Jun. 18, 1992

[51] Int. Cl.$^5$ ............................................. C07D 305/14
[52] U.S. Cl. ..................................... 549/510; 549/511
[58] Field of Search ................................. 549/510, 511

[56] References Cited

U.S. PATENT DOCUMENTS 4,243,594  1/1981  Beale et al. ........................ 549/297

OTHER PUBLICATIONS

Gamini Samaranayake et al, "Modified Taxols. 5. Reaction of Taxol with Electrophilic Reagents and Preparation of a Rearranged Taxol Derivative with Tubulin Assembly Activity," *Journal of Organic Chemistry*, 1991, vol. 56, pp. 5114–5119.

N. N. Yarovenko et al, "Fluorination by Means of α-Fluorinated Amines," *Journal of Organic Chemistry USSR* (English), 1959, vol. 29, pp. 2125–2128.

Lawrence H. Knox et al, "Steroids. CCXL. The Reaction of Steroidal Alcohols with 2-Chloro-1,1,2-trifluorotriethylamine," *Journal of Organic Chemistry*, Aug. 1964, vol. 29, pp. 2187–2195.

David G. I. Kingston et al, "The Chemistry of Taxol, A Clinically Useful Anticancer Agent," *Journal of Natural Products*, Jan.–Feb. 1990, vol. 53, No. 1, pp. 1–12.

*Primary Examiner*—C. Warren Ivy
*Assistant Examiner*—Ba K. Trinh
*Attorney, Agent, or Firm*—Mollie M. Yang

[57] ABSTRACT

The present invention relates to 10-desacetoxy-11,12-dihydrotaxol-10,12(18)-diene derivatives which are useful as antitumor agents and as intermediates for the preparation of 10-desacetoxytaxol. Also disclosed is a novel process for the preparation of 10-desacetoxytaxol which comprises treating hydroxy protected 10-deacetyltaxol with 1,1,2-trifluoro-2-chlorotriethylamine followed by catalytic hydrogenation.

7 Claims, No Drawings

TAXOL DERIVATIVES

BACKGROUND OF THE INVENTION

The present invention relates to novel antitumor agents, process for their preparation, and intermediates useful therein. More particularly, the present invention relates to 10-desacetoxytaxol derivatives which are useful as intermediates in the preparation of 10-desacetoxytaxol.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds of the present invention.

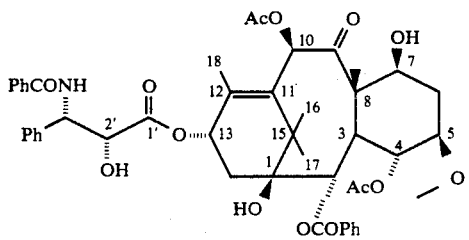

SUMMARY OF THE INVENTION

The present invention relates in one aspect to 10-desacetoxy taxol derivatives of formula (I)

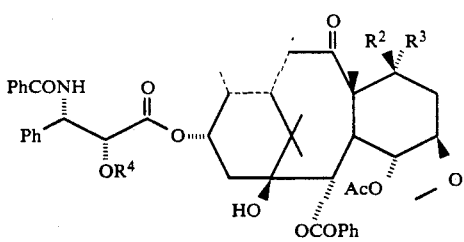

wherein $R^2$ is hydrogen and $R^3$ is hydroxy; or $R^3$ is hydrogen and $R^2$ is hydroxy, chlorofluoroacetoxy, or a protected hydroxy group; $R^4$ is hydrogen or a hydroxy protecting group; and the dash bonds together represent 10,12-diene or 11-ene; with the proviso that when $R^3$ is hydroxy and $R^2$ is hydrogen, or when $R^3$ is hydrogen and $R^2$ is hydroxy or a protected hydroxy group, the dash bonds together represent 10,12-diene.

Another aspect of the present invention provides a process for the preparation of a compound having the formula

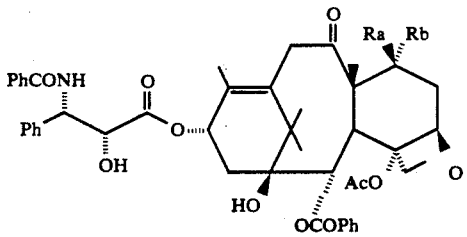

wherein $R^a$ is hydrogen and $R^b$ is hydroxy, or $R^a$ is hydroxy and $R^b$ is hydrogen, which comprises: 1) reacting a compound of the formula

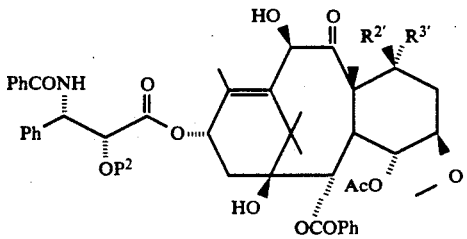

wherein $R^{2'}$ is $OP^2$ and $R^{3'}$ is hydrogen, or $R^{2'}$ is hydrogen and $R^{3'}$ is hydroxy, and $P^2$ is a hydroxy protecting group, with 1,1,2-trifluoro-2-chlorotriethylamine to provide a compound having the formula

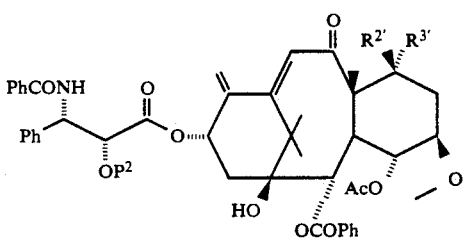

2) hydrogenating the product of step 1) in the presence of a catalyst; and 3) removing the hydroxy protecting groups.

Another aspect of the present invention provides a process for the preparation of 7-O-(chlorofluoroacetyl)-10-desacetoxytaxol which comprises: 1) reacting a 2'-hydroxy protected 10-deacetyltaxol with 1,1,2-trifluoro-2-chlorotriethylamine to provide the corresponding 2'-hydroxy protected-7-O-(chlorofluoroacetyl)-11,12-dihydrotaxol-10,12(18)diene; 2) hydrogenating the product of step 1) in the presence of a catalyst; and 3) removing the hydroxy protecting group.

DETAILED DESCRIPTION OF THE INVENTION

As used herein "Ph" means phenyl; "Ac" means acetyl; "11-ene" means a double bond between carbon atoms 11 and 12 of a compound of formula (I) or formula (II); and "10,12-diene" means double bonds between carbon atoms 10 and 11, and 12 and 18 of a compound of formula (I) or formula (II). Hydroxy protecting group includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but are not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$-alkoxy, or nitro.

The present invention provides in one aspect novel 10-desacetoxytaxol derivatives of the formula (I)

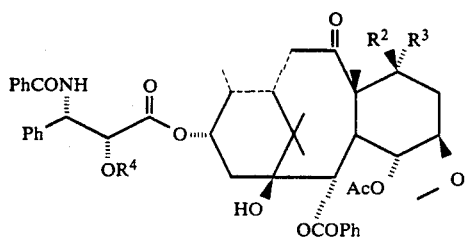

wherein $R^2$ is hydrogen and $R^3$ is hydroxy, or $R^3$ is hydrogen and $R^2$ is hydroxy, chlorofluoroacetoxy, or a protected hydroxy group; $R^4$ is hydrogen or a hydroxy protecting group; and the dash bonds together represent 10,12-diene or 11-ene; with the proviso that when $R^3$ is hydroxy and $R^2$ is hydrogen, or when $R^3$ is hydrogen and $R^2$ is hydroxy or a protected hydroxy group, the dash bonds together represent 10,12-diene.

In one preferred embodiment of compounds of formula (I), $R^2$ is hydrogen and $R^3$ is hydroxy, or $R^3$ is hydrogen and $R^2$ is hydroxy, chlorofluoroacetoxy, or a protected hydroxy group; $R^4$ is hydrogen or a hydroxy protecting group; and the dash bonds together represent 10,12-diene. In another preferred embodiment, $R^2$ is chlorofluoroacetoxy, $R^3$ is hydrogen, $R^5$ is phenyl, $R^4$ is hydrogen or a hydroxy protecting group, and the dash bonds together represent 10,12-diene or 11-ene. In another preferred embodiment, $R^2$ is hydroxy or a protected hydroxy group, and $R^3$ is hydrogen; or $R^2$ is hydrogen and $R^3$ is hydroxy; $R^4$ is hydrogen or a hydroxy protecting group; and the dash bonds together represent 10,12-diene or 11-ene. Where $R^4$ is a hydroxy protecting group, it is preferably one of the carbonate type, most preferably it is selected from the group consisting of 2,2,2-trichloroethoxycarbonyl, allyloxycarbonyl, and benzyloxycarbonyl.

The most preferred embodiments of compounds of formula (I) are: 1) 2'-O-allyloxycarbonyl-7-O-chlorofluoroacetyl-10-desacetoxy-11,12-dihydrotaxol-10,12(18)-diene; 2) 7-O-chlorofluoroacetyl-10-desacetoxy-11,12-dihydrotaxol-10,12(18)-diene; 3) 7-O-chlorofluoroacetyl-10-desacetoxytaxol; 4) 2'-O-benzyloxycarbonyl-7-chlorofluoroacetyl-10-desacetoxy-11,12-dihydrotaxol-10,12(18)-diene; 5) 2',7-bis-O-(2,2,2-trichloroethoxycarbonyl)-10-desacetoxy-11,12-dihydrotaxol-10,12(18)-diene; 6) 10-desacetoxy-11,12-dihydrotaxol-10,12(18)-diene; 7) 2'-O-benzyloxycarbonyl-10-desacetoxy-11,12-dihydrotaxol-10,12(18)-diene; 8) 2'-O-allyloxycarbonyl-10-desacetoxy-11,12-dihydro-7-epitaxol-10,12(18)-diene; and 9) 10-desacetoxy-11,12-dihydro-7-epitaxol-10,12(18)-diene.

The starting materials used for the preparation of compounds of formula (I) are 10-deacetyltaxol and 10-deacetyl-7-epitaxol which may be obtained from taxol by treating the latter with zinc bromide in chloroform/methanol as reported in G. Samaranayake et al, *J. Org. Chem.*, 1991, 56:5114-5119, hereby incorporated by reference.

The present invention provides in one embodiment compounds of formula (I) wherein $R^3$ is hydrogen and $R^2$ is chlorofluoroacetoxy which may be prepared from 10-deacetyltaxol by following the reaction sequence depicted in Scheme I.

SCHEME I

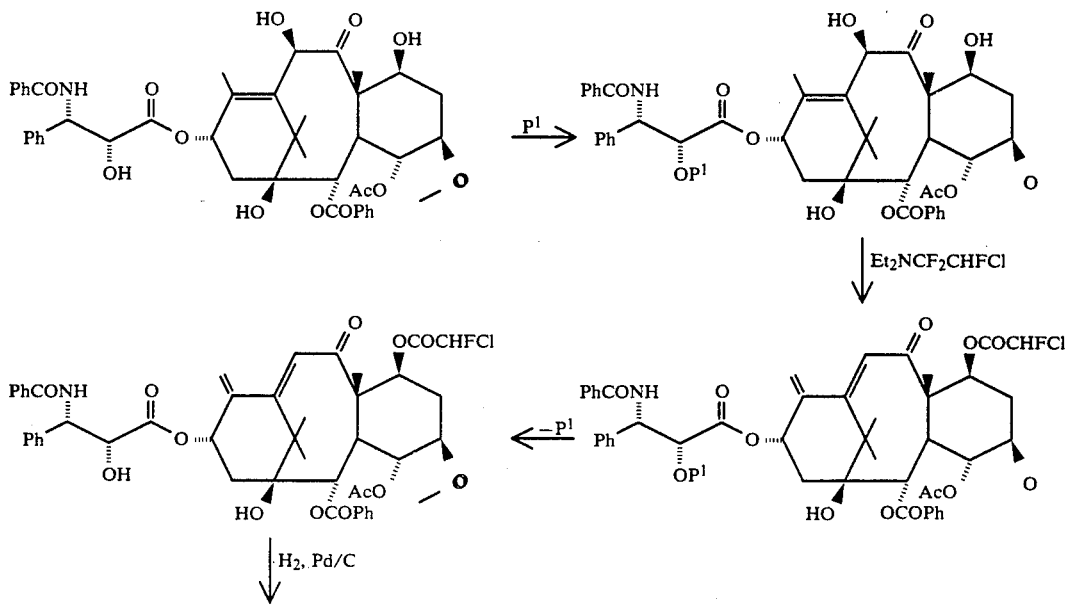

SCHEME I

-continued

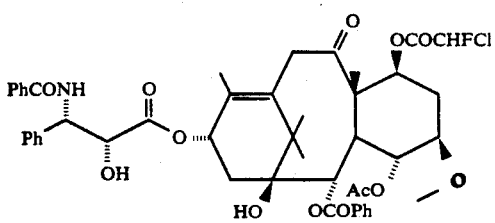

In Scheme I, P¹ is a hydroxy protecting group. Thus in the first reaction step, the 2'-hydroxy group of 10-deacetyltaxol is protected; the protecting group may be one that can be introduced and removed without unacceptably affecting the rest of the molecule, more preferably it may be one that preferentially blocks the 2'-hydroxy group over the two secondary hydroxy groups on the ring, namely, the 7- and 10-hydroxy groups. Protection of a hydroxy group may be accomplished by methods well known in the art; for example, reacting with a carboxylic acid or its acylating equivalent to form an ester, reacting with an alkyl halide in the presence of a base to form an ether, or reacting with a chloroformate to form the carbonate.

The preferred 2'-hydroxy protecting group in this reaction is a carbonate which can be formed by treating 10-deacetyltaxol with an appropriate chloroformate, for example, allyl or benzyl chloroformate to form the corresponding carbonate. The reaction is carried out in an inert organic solvent such as dichloromethane, tetrahydrofuran, acetonitrile, dimethylformamide, benzene, pyridine, p-dioxan, and preferably in the presence of an acid scanvenger such as an amine base, for example, pyridine, diisopropylethylamine, 4-aminopyridine, triethylamine and the like, or an inorganic base such as potassium carbonate or tetrabutylammonium hydroxide, at a suitable temperature which may be from −78° C. to about 50° C., depending on the particular reagents chosen. Generally from about one to ten equivalents of the protecting group reagent relative to the taxol compound may be used; it is advantageous to monitor the reaction for example by thin-layer chromatography so as to achieve the desired degree of protection.

The 2'-hydroxy protected 10-deacetyltaxol thus obtained is then treated with 1,1,2-trifluoro-2-chlorotriethylamine (hereinafter TFCT) to give 2'-hydroxy protected 7-O-chlorofluoroacetyl-10-desacetoxy-11,12-dihydrotaxol-10,12(18)-diene. TFCT can be prepared from diethylamine and trifluorochloroethylene according to the method reported in N. N. Yarovenko, *J. Org. Chem. USSR* (English), 1959, 29:2125-8, hereby incorporated by reference. The reaction of 2'-hydroxy protected 10-deacetyltaxol and TFCT is carried out in an inert organic solvent such as halogenated hydrocarbons, for example, dichloromethane, chloroform, and carbon tetrachloride, at a temperature of from about 0° C. up to the refluxing temperature of the reaction solution, preferably the reaction is run at ambient temperature. The TFCT is used in at least 1 equivalent to the taxol reactant, but preferably it is used in excess; typically from about one to about ten equivalents of TFCT may be used relative to the taxol reactant.

The 2'-hydroxy protecting group can be removed using methods known in the art that are suitable for the particular protecting group used; for example, acid or base catalyzed hydrolysis, reduction, hydrogenolysis, and the like. Thus the allyl carbonate can be removed by tributyltin hydride and tetrakis(triphenylphosphine)-palladium; the benzyl carbonate can be removed by catalytic hydrogenolysis.

7-O-Chlorofluoroacetyl-10-desacetoxy-11,12-dihydrotaxol-10,12(18)-diene can be converted to 10-desacetoxy-7-O-chlorofluoroacetyltaxol by catalytic hydrogenation in which the catalyst may be for example palladium, platinum, rhodium and the like. In cases where the 2'-hydroxy protecting group used in the previous steps of the reaction sequence is benzyloxycarbonyl, catalytic hydrogenation converts the 10,12-diene into the 11-ene, and removes the protecting group in one step. It is understood that the order of deprotecting the 2'-hydroxy group and hydrogenation is not crucial, and either may be effected prior to the other.

A further embodiment of the present invention provides compounds of formula (I) wherein $R^2$ is hydrogen and $R^3$ is hydroxy, or $R^3$ is hydrogen and $R^2$ is hydroxy or protected hydroxy; and the dash bonds together represent 10,12-diene. The preparation of compounds of this type from 10-deacetyltaxol or 10-deacetyl-7-epitaxol, as well as their conversion to 10-desacetoxy taxol or 10-desacetoxy-7-epitaxol, is depicted in Scheme II.

SCHEME II

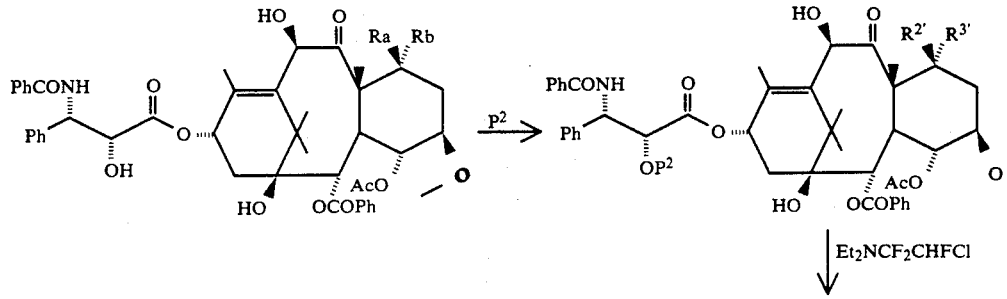

-continued
SCHEME II

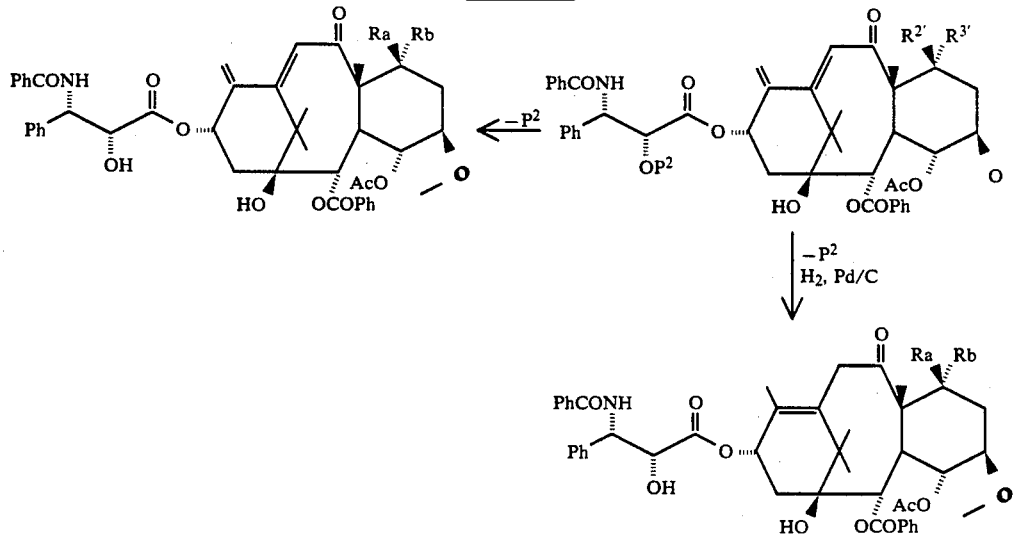

In Scheme II, $R^a$ is hydroxy, $R^b$ is hydrogen, $R^{2'}$ is $OP^2$, and $R^{3'}$ is hydrogen; or $R^a$ is hydrogen, $R^b$ is hydroxy, $R^{2'}$ is hydrogen, and $R^{3'}$ is hydroxy; $P^2$ is a hydroxy protecting group. When 10-deacetyltaxol (i.e. $R^a$ is hydroxy and $R^b$ is hydrogen) is the starting material, it is desirable to protect both the 2'- and the 7-hydroxy groups, and that the 10-hydroxy group be left free; preferably the protecting group is 2,2,2-trichloroethoxycarbonyl which can be introduced by reacting the taxol reactant with 2,2,2-trichloroethyl chloroformate in the presence of a base such as pyridine, diisopropylamine, triethylamine, dimethylaminopyridine, and the like. To control the degree of protection and to minimize blocking the 10-hydroxy group, the base is usually used in about one to two equivalents relative to taxol and the chloroformate in about 0.6 to about 1.5 equivalents relative to taxol. When 10-deacetyl-7-epitaxol (i.e. $R^a$ is hydrogen and $R^b$ is hydroxy) is the starting material, only the 2'-hydroxy group is protected since the 7-hydroxy group is substantially more inert than the 2'-hydroxy group, and is relatively insusceptible to acylation, either with a chloroformate, or with the TFCT in the subsequent step.

The 2',7-bishydroxy protected 10-deacetyltaxol or 2,-hydroxy protected 10-deacetyl-7-epitaxol thus obtained is then treated with TFCT to give 2',7-bishydroxy protected 10-desacetoxy-11,12-dihydrotaxol-10,12(18)-diene or 2'-protected 10-desacetoxy-11,12-dihydro-7-epitaxol-10,12(18)-diene, respectively. The reaction with TFCT is carried out in an inert organic solvent such as halogenated hydrocarbons such as dichloromethane, chloroform and carbon tetrachloride, at a temperature of from about 0° C. to about the refluxing temperature of the reaction solution, preferably the reaction is run at ambient temperature. The TFCT is used in at least 1 equivalent to the taxol reactant, but preferably it is used in excess; typically TFCT is used from about one to about ten equivalents. The 2'- and, if present, the 7-hydroxy protecting group is then removed using method suitable for the particular protecting group to provide 10-desacetoxy-11,12-dihydrotaxol-10,12(18)-diene or 10-desacetoxy-11,12-dihydro-7-epitaxol-10,12(18)-diene; for example, trichloroethyoxycarbonyl group is removed by a zinc reagent, benzyloxycarbonyl is removed by hydrogenolysis, and allyl carbonate is removed by tributyltin hydride and tetrakis(triphenylphosphine)palladium. 10-Desacetoxy-11,12-dihydrotaxol-10,12(18)-diene and 10-desacetoxy-11,12-didehydro-7-epitaxol-10,12(18)-diene may then be subjected to catalytic hydrogenation as previously discussed to provide 10-desacetoxytaxol and 10-desacetoxy-7-epitaxol, respectively.

2',7-Bishydroxy protected 10-desacetoxy-11,12-dihydrotaxol-10,12(18)-diene or 2'-hydroxy protected 10-desacetoxy-11,12-dihydro-7-epitaxol-10,12(18)-diene can also be subjected to catalytic hydrogenation to give 2',7-bishydroxy protected 10-desacetoxytaxol or 2'-hydroxy protected 10-desacetoxy-7-epitaxol, respectively. The hydroxy protecting groups may be removed as previously described to provide 10-desacetoxytaxol or 10-desacetoxy-7-epitaxol.

The 10-desacetoxytaxol derivatives of the present invention are useful agents for inhibiting tumor growth in animals and human. Compounds were evaluated in in vitro cytotoxicity activity against human colon carcinoma cells HCT-116 and HCT-116/VM46. The HCT116/VM cells are cells that have been selected for teniposide resistance and express the multidrug resistance phenotype, including resistance to taxol. Cytotoxicity was assessed in HCT-116 human colon carcinoma cells by XTT (2,3-bis(2-methoxy-4-nitro-5-sulfophenyl)-5-[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines," *Cancer Res.* 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an $IC_{50}$, which is the drug concentration required to inhibit cell proliferation (i.e., absorbance at 450 nm) to 50% of that of untreated control cells. The $IC_{50}$ values for compounds evaluated in this assay are given in Table I.

TABLE I

In vitro cytotoxicity for taxol analogs against human colon carcinoma cells.

| Compound | IC$_{50}$ ($\mu$M) HCT-116 | HCT-116/VM46 |
|---|---|---|
| Example 3 | 0.038 | 1.95 (51)* |
| Example 4 | 0.008 | 1.26 (158) |
| Example 9 | 0.038 | 0.860 (23) |
| Example 10 | 0.008 | 1.22 (153) |
| Example 13 | >0.098 | 3.09 (<32) |
| Example 16 | 0.040 | 0.855 (21) |
| Taxol | 0.004 | 0.440 (124) |

*Value is parenthesis is fold resistance relative to HCT-116 cells.

Compounds of formula (I) of the instant invention are useful for inhibiting tumor growth in animals including humans and are preferably administered in the form of a pharmaceutical composition comprising an effective antitumor amount of compound of the instant invention in combination with a pharmaceutically acceptable carrier or diluent.

Antitumor compositions herein may be made up in any suitable form appropriate for desired use; e.g., oral, parenteral or topical administration. Examples of parenteral administration are intramuscular, intravenous, intraperitoneal, rectal and subcutaneous administration.

The diluent or carrier ingredients should not be such as to diminish the therapeutic effects of the antitumor compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by unknown techniques; e.g., to delay disintegration and absorption. Inert diluents and carriers which may be used in capsules include, for example, calcium carbonate, calcium phosphate and kaolin. Suspensions, syrups and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions and the like. They may also be manufactured in the form of sterile solid compositions which can be dissolved or suspended in sterile injectable medium immediately before use. They may contain suspending or dispersing agents known in the art.

One aspect of the invention herein is directed to therapeutically inhibiting tumor growth in an animal host having a tumor sensitive to the compounds of the instant invention which comprises administering to said host an effective antitumor dose of said compound. It will be appreciated that the actual preferred amount of compound of the instant invention used will vary according to the particular compound, the particular composition formulated, the mode of application and the particular situs, host and disease being treated. Many factors that modify the action will be taken into account by those skilled in the art; e.g., age, body weight, sex, diet, time of administration, route of administration, rate of excretion, condition of the host, drug combinations, reaction sensitivities and severities and severity of disease. Administration can be carried out continuously or periodically within the maximum tolerated dose. Optimal application rates for a given set of conditions can be ascertained by those skilled in the art using conventional dosage administration tests in view of the above guidelines.

The following examples are provided in order to more fully illustrate the present invention, and are not to be construed as limiting in any manner the scope of the invention which is defined by the claims.

EXAMPLE 1

2'-O-allyloxycarbonyl-10-deacetyl taxol (1)

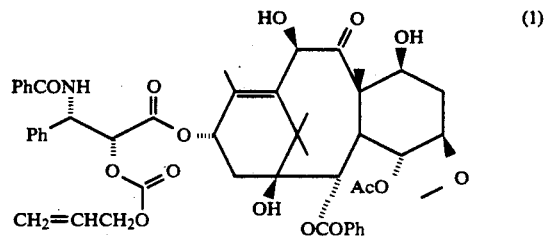

A solution of 10-deacetyl taxol [see Samaranayake, G. et al "Modified Taxols. 5 . . . ," *J. Org. Chem.*, 1991, 56:5114–5119] (262 mg, 0.323 mmol) in dry dichloromethane (10 mL) was treated with pyridine (0.130 mL, 1.62 mmol), followed by allyl chloroformate (0.103 mL, 0.969 mmol). After addition of a trace (1–2 mg) of 4-dimethylaminopyridine, the mixture was stirred at room temperature for 3 h, then more allyl chloroformate (0.033 mL) was added. After a further 12 h period at room temperature, the mixture was diluted with dichloromethane (100 mL), and the organic phase was washed with water (3×10 mL) and brine (10 mL). Drying and evaporation gave a crude product that was purified by silica gel chromatography (60% ethyl acetate in hexane). Yield: 165 mg (57%) of a white foam. NMR (300 MHz, CDCl$_3$)$\delta$ 8.13 (d, J=8.5 Hz, 2H) 7.74 (d, J=8.2 Hz, 2H) 7.63 (m, 11H) 6.98 (exch. d, J=9.3 Hz, 1H) 6.27 (br t, 1H) 5.97 (dd, J=9.3 Hz, J'=2.5 Hz, 1H) 5.87 (m, 1H) 5.68 (d, J=7.1 Hz, 1H) 5.43 (d, J=2.5 Hz, 1H) 5.38–5.26 (m, 2H) 5.20 (s, 1H) 4.94 (d, J=7.8 Hz, 1H) 4.62 (m, 2H) 4.40–4.18 (m, 4H) 3.91 (d, J=7.1 Hz, 1H) 2.61–1.67 (m, 15H, incl. singlets at 2.46, 1.92, 1.73, 3H each) 1.13 (s, 3H) 1.10 (s, 3H). High Res. Mass Spectrum: Calcd for C$_{49}$H$_{53}$NO$_{15}$K (MK+) 934.3052, found 934.3041.

EXAMPLE 2

2'-O-allyloxycarbonyl-7-O-chlorofluoroacetyl-10-desacetoxy-11,12-dihydrotaxol-10,12(18)-diene (2)

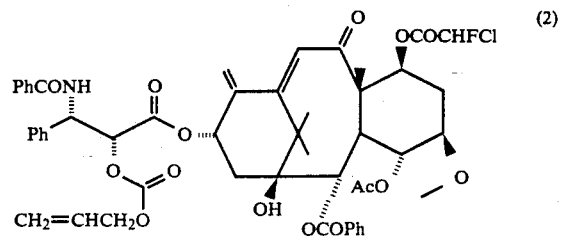

A solution of 1 (49 mg, 0.055 mmol) in dry dichloromethane (1.5 mL) was treated at room temperature with 1,1,2-trifluoro-2-chlorotriethylamine (TFCT, 0.035 mL, 0.219 mmol). After stirring for 3 h, the solvent was removed in vacuo and the residue was chromatographed on silica gel (30% ethyl acetate in hexane) to afford dienone 2 (20 mg, 37% yield) as a white solid. NMR (300 MHz, CDCl$_3$)δ 8.18 (d, J=8.6 Hz, 2H) 7.68 (d, J=8.2 Hz, 2H) 7.63–7.25 (m, 11H) 6.91 (exch.d, J=9.6 Hz, 1H) 6.34–6.17 (m, 3H) 5.97 (dd, J=9.6 Hz, J'=2.2 Hz, 1H) 5.95–5.90 (m, 1H) 5.79 (d, J=7.8 Hz, 1H) 5.52 (dd, J=10.6 Hz, J'=7.4 Hz, 1H) 5.49–5.24 (m, 4H) 5.03 (d, J=1.9 Hz, 1H) 4.96 (d, J=9.0 Hz, 1H) 4.67–4.56 (m, 2H) 4.29 (AB q, 2H) 3.74 (d, J=7.8 Hz, 1H) 2.61–1.01 (m, 17 H).

High Res. Mass Spectrum: Calcd for C$_{51}$H$_{52}$NO$_{15}$ClF (MH+) 972.3010, found 972.3032.

EXAMPLE 3

7-O-chlorofluoroacetyl-10-desacetoxy-11,12-dihydrotaxol-10,12(18)-diene (3)

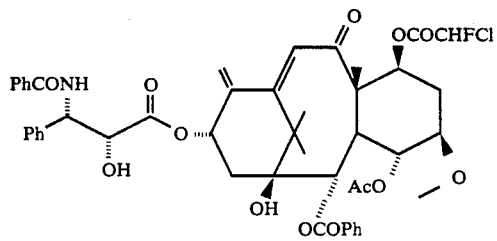

Dienone 2 (40.7 mg, 0.042 mmol) in dry THF (1 mL) was treated with a solution of tetrakis(triphenylphosphine)palladium in dichloromethane (0.042M, 0.01 mL), then with acetic acid (0.012 mL, 0.21 mmol) and tributyltin hydride (0.0225 mL, 0.084 mmol). After 30 min at room temperature, the solvent was removed and the residue was dissolved in acetonitrile (6 mL) and washed 3 times with hexane (5 mL each). The acetonitrile layer was evaporated and the residue chromatographed (silica gel, 40% ethyl acetate in hexane) to afford 3 (25.8 mg, 70%) as a colorless foam. NMR (300 MHz, CDCl$_3$) δ 8.18 (d, J=8.6 Hz, 2H) 7.68 (d, J=8.2 Hz, 2H) 7.66–7.20 (m, 11H) 6.91 (exch. d, J=9.4 Hz, 1H) 6.33–6.16 (m, 3H) 5.81–5.71 (m, 2H) 5.52 (dd, J=10.6 Hz, J'=7.4 Hz, 1H) 5.18 (d, J=1.9Hz, 1H) 4.95 (d, J=8.0 Hz, 1H) 4.78 (d, J=1.9 Hz, 1H) 4.73 (dd, J=4.3 Hz, J'=2.1 Hz, 1H) 4.26 (AB q, 2H) 3.74 (d, J=7.8 Hz, 1H) 3.60 (exch. d, J=4.3 Hz, 1H) 2.58–1.01 (m, 17H). High Res. Mass Spectrum: Calcd for C$_{47}$H$_{48}$NO$_{13}$ClF (MH+) 888.2798, found 888.2775.

EXAMPLE 4

7-O-chlorofluoroacetyl-10-desacetoxytaxol (4)

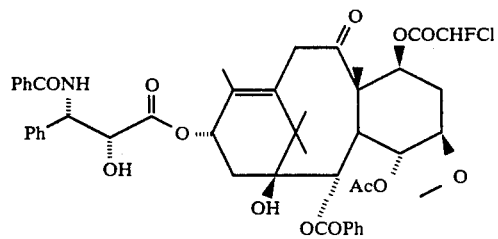

Dienone 3 (25 mg, 0.028 mmol) was dissolved in ethyl acetate (1 mL) and treated with palladium on charcoal (10%, 15 mg, 0.014 mmol). The slurry was stirred under an atmosphere of hydrogen at room temperature for 12 h. The catalyst was filtered off, the filtrate concentrated and chromatographed (silica gel, 40% ethyl acetate in hexane) to afford 4 as a white solid (15.1 mg, 60%). NMR (300 MHz, CDCl$_3$)δ 8.10 (d, J=8.5 Hz, 2H) 7.73 (d, J=8.4 Hz, 2H) 7.63–7.26 (m, 11H) 7.03 (exch.d, J=9.4 Hz, 1H) 6.19 (d, J$_{HF}$=52.5 Hz, 1H) 6.10 (br t, 1H) 5.77 (dd, J=9.5 Hz, J'=2.2 Hz, 1H) 5.67–5.63 (m, 2H) 4.92 J=7.7 Hz, 1H) 4.77 (d, J=2.2 Hz, 1H) 4.25 (AB q, H) 4.11 (d, J=6.6 Hz, 1H) 3.90 (d, J=16.2 Hz, 1H) 3.54 (exch. br s, 1H) 3.33 (br d, J=16.2 Hz, 1H) 2.56 (m, 1H) 2.40–1.10 (m, 19H, incl. singlets at 2.37, 1.74, 1.72, 1.15, 1.10, 3H each). High Res. Mass Spectrum Calcd for C$_{47}$H$_{50}$NO$_{13}$ClF (MH+) 890.2955, found 890.2946.

EXAMPLE 5

2'-O-benzyloxycarbonyl 10-deacetyl taxol (5)

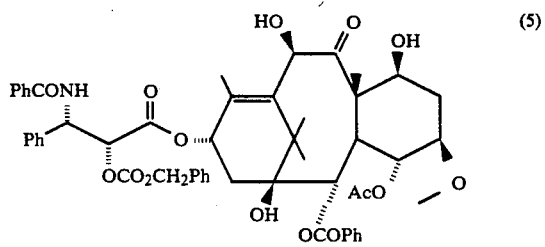

A solution of 10-deacetyl taxol (207 mg, 0.255 mmol) in dry dichloromethane (4 mL) was treated at 0° C. with diisopropylethylamine (0.115 mL, 0.657 mmol) and benzyl chloroformate (0.094 mL, 0.657 mmol). The solution was stirred for 5.5 h at room temperature then worked up as in Example 1. Silica gel chromatography (55% ethyl acetate in hexane) gave 5 as a colorless oil (211 mg, 87%). NMR (300 MHz, CDCl$_3$)δ 8.12 (d, J=8.5 Hz, 2H) 7.68 (d, J=8.2 Hz, 2H) 7.61–7.30 (m, 16H) 6.95 (exch. d, J=9.2 Hz, 1H) 6.25 (br t, 1H) 5.95 (dd, J=9.3 Hz, J'=2.6 Hz, 1H) 5.67 (d, J=7.2 Hz, 1H) 5.44 (d, J=2.6 Hz, 1H) 5.20–5.10 (m, 3H) 4.92 (d, J=7.7 Hz, 1H) 4.32–4.18 (m, 4H) 3.90 (d, J=7.2 Hz, 1H) 2.60–1.70 (m, 15H, incl. singlets at 2.42, 1.90, 1.72, 3H each) 1.18 (s, 3H) 1.10 (s, 3H).

High Res. Mass Spectrum: Calcd for C$_{53}$H$_{56}$NO$_{15}$ (MH+) 946.3650, found 946.3641.

EXAMPLE 6

2'-O-benzyloxycarbonyl-7-chlorofluoroacetyl-10-desacetoxy-11,12-dihydrotaxol-10,12(18)-diene (6)

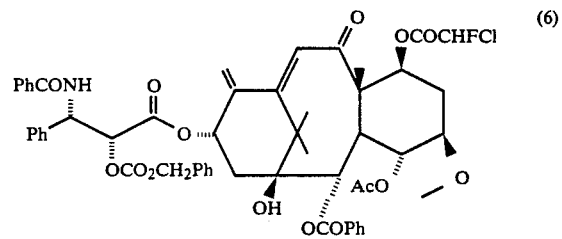

A solution of benzyl carbonate 5 (55.5 mg, 0.059 mmol) in dry dichloromethane (1.2 mL) was treated at room temperature with TFCT (0.0378 mL, 0.235 mmol). After 3 h at room temperature, work-up as in Example 2 gave 6 as a white solid (24.6 mg, 41%). NMR (300 MHz, CDCl$_3$)δ 8.12 (d, J=8.5 Hz, 2H) 7.68 (d, J=8.2 Hz, 2H) 7.58–7.24 (m,16H) 6.89 (exch.d, J=9.7 Hz, 1H) 6.25 (d, J$_{HF}$=50.2 Hz, 1H) 6.24 (br t, 1H) 6.22 (s, 1H)

5.97 (dd, J=9.7 Hz, J'=2.2 Hz, 1H) 5.80 (d, J=7.8 Hz, 1H) 5.52 (dd, J=10.8 Hz, J'=7.3 Hz, 1H) 5.43 (d, J=2.2 Hz, 1H) 5.38 (d, J=2 Hz, 1H) 5.14 (AB q, 2H) 5.02 (d, J=2 Hz, 1H) 4.96 (d, J=7.7 Hz, 1H) 4.31 (AB q, 2H) 3.75 (d, J=7.8 Hz, 1H) 2.55 (m, 1H) 2.46 (s, 3H) 2.15-2.04 (m, 3H) 1.82 (s, 3H) 1.23 (s, 1H) 1.12 (s, 3H) 1.09 (s, 3H).

Hydrogenation of 6 according to the procedure of Example 4 gave directly 4.

EXAMPLE 7

2',7-bis-O-(2,2,2-trichloroethoxycarbonyl)-10-deacetyl taxol (7)

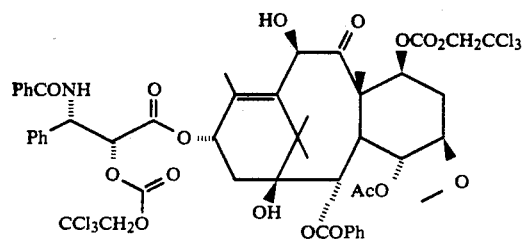

(7)

10-Deacetyl taxol (140 mg, 0.173 mmol) in dry dichloromethane (3.5 mL) was treated at 0° C. with pyridine (0.028 mL, 0.346 mmol) and trichloroethyl chloroformate (0.0724 mL, 0.260 mmol). After 1 h at this temperature, the cold bath was removed and the mixture was stirred at room temperature overnight. The solvent was evaporated and the residue chromatographed on silica gel (30-50% ethyl acetate in hexane) to afford 7 as a foam (92.3 mg, 46%). Further elution afforded unreacted starting material (35 mg, 25%). Carbonate 7 had NMR (300 MHz, CDCl$_3$)δ 8.14 (d, J=8.5 Hz, 2H) 7.75 (d, J=8.5 Hz, 2H) 7.65-7.35 (m, 11H) 6.94 (exch.d, J=9.3 Hz, 1H) 6.27 (br t, 1H) 6.04 (dd, J=9.3 Hz, J'=2.6 Hz, 1H) 5.71 (d, J=6.9 Hz, 1H) 5.54 (d, J=2.6 Hz, 1H) 5.43-5.37 (m, 2H) 4.96 (d, J=7.9 Hz, 1H) 4.85-4.67 (m, 4H) 4.29 (AB q, 2H) 4.04-4.01 (m, 2H) 2.69-1.80 (m, 14H incl. singlets at 2.58, 1.96, 1.89, 3H each) 1.20 (s, 3H) 1.09 (s, 3H).

High Res. Mass Spectrum: Calcd for C$_{51}$H$_{51}$NO$_{17}$Cl$_6$K (MK+) 1198.0925, found 1198.0949.

EXAMPLE 8

2',7-bis-O-(2,2,2-trichloroethoxycarbonyl)-10-desacetoxy-11,12-dihydrotaxol-10,12(18)-diene (8)

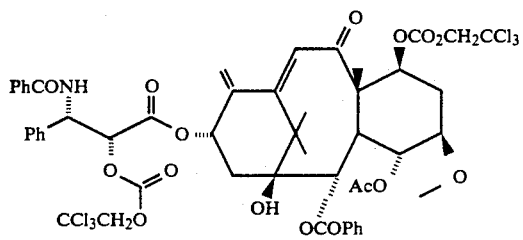

(8)

Bis-carbonate 7 (92.3 mg, 0.079 mmol) in dry dichloromethane (2 mL) was treated at room temperature with TFCT (0.0384 mL, 0.238 mmol). The solution was stirred overnight. The solvent was evaporated and the residue purified by column chromatography (25% ethyl acetate in hexane) to afford 8 as a white powder (42.8 mg, 47.3%). NMR (300 MHz, CDCl$_3$)δ 8.18 (d, J=8.5 Hz, 2H) 7.69 (d, J=8.5 Hz, 2H) 7.58-7.28 (m, 11H) 6.90 (exch. d, J=9.7 Hz, 1H) 6.31 (s, 1H) 6.25 (br t, 1H) 6.04 (dd, J=9.7 Hz, J'=2.2 Hz, 1H) 5.80 (d, J=7.8 Hz, 1H) 5.51 (d, J=2.2 Hz, 1H) 5.38 (d, J=2.3 Hz, 1H) 5.31 (dd, J=11.0 Hz, J'=7.3 Hz, 1H) 4.99 (d, J=2.3 Hz, 1H) 4.97 (br d, 1H) 4.80-4.65 (m, 4H) 4.30 (AB q, 2H) 3.75 (d, J=7.8 Hz, 1H) 2.60 (m, 1H) 2.55 (s, 3H) 2.16-2.09 (m, 3H) 1.83 (s, 3H) 1.77 (s, 1H) 1.13 (s, 3H) 1.07 (s, 3H).

High Res. Mass Spectrum: Calcd for C$_{51}$H$_{49}$NO$_{16}$Cl$_6$K (MK+) 1180.0820, found 1180.0777.

EXAMPLE 9

10-Desacetoxy-11,12-dihydrotaxol-10,12(18)-diene (9)

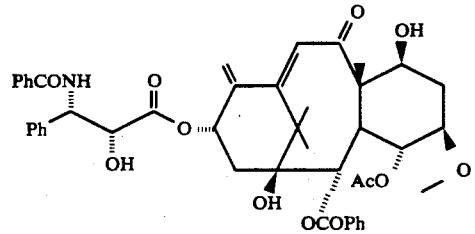

(9)

Dienone 8 (180 mg, 0.157 mmol) was dissolved in methanol (3 mL) and treated with acid-washed Zn dust (300 mg, 4.72 mmol). The slurry was refluxed for 20 min, filtered, and the filtrate evaporated. Chromatography of the residue (40-60% ethyl acetate in hexane) gave 9 as a foam (18 mg, 14%), together with its 7-epi isomer 10 (97 mg, 77.7%). Compound 9 had NMR (300 MHz, CDCl$_3$)δ 8.19 (d, J=8.5 Hz, 2H) 7.69 (d, J=8.5 Hz, 2H) 7.59-7.25 (m, 11H) 7.00 (exch. d, J=10.4 Hz, 1H) 6.20 (br t, 1H) 5.96 (s, 1H) 5.83-5.77 (m, 2H) 5.18 (d, J=2.2 Hz, 1H) 4.94 (dd, J=7.2 Hz, J'=2.1 Hz, 1H) 4.79 (d, J=2.2 Hz, 1H) 4.72 (dd, J=4.3 Hz, J'=2.2 Hz, 1H) 4.30 (AB q, 2H) 4.00 (m, 1H) 3.65 (d, J=7.8 Hz, 1H) 3.51 (exch. d, J=4.3 Hz, 1H) 2.60 (m, 1H) 2.40 (s, 3H) 2.30-1.80 (m, 5H) 1.70 (s, 3H) 1.16 (s, 3H) 1.06 (s, 3H).

High Res. Mass Spectrum: Calcd for C$_{45}$H$_{48}$NO$_{12}$ (MH+) 794.3177, found 794.3152.

Alternatively, dienone 8 (39 mg, 0.034 mmol) was dissolved in methanol (0.5 mL) and acetic acid (0.5 mL), and treated with acid-washed zinc dust (66.4 mg, 1.020 mmol). The slurry was heated at 40° C. for 1 h, filtered and the filtrate evaporated. Chromatography of the residue with 60% ethyl acetate/hexane gave 9 as a foam (22 mg, 81%). Spectral data are the same as the previous ones.

EXAMPLE 10

10-Desacetoxytaxol (17)

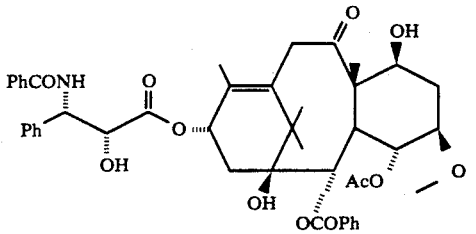

(17)

Dienone 9 (22 mg, 0.028 mmol) in ethyl acetate (0.7 mL) was hydrogenated at atmospheric pressure in the presence of palladium on charcoal (10%, 14.7 mg, 0.014 mmol Pd) After 5.5 h at RT, filtration (rinsing with ethyl acetate), evaporation and chromatography (60% ethyl acetate in hexane) gave 10-deoxytaxol 17 (15.0 mg, 68%) as a white foam. NMR (CDCl3)δ 8.12(d, J=8.5 Hz, 2H) 7.61 (d, J=8.4 Hz, 2H) 7.60-7.27 (m, 11H) 7.06 (exch. d, J=8.9 Hz, 1H) 6.09 (br t, 1H) 5.78 (dd, J=8.9 Hz, J'=2.6 Hz, 1H) 5.66 (d, J=6.8 Hz, 1H) 4.91 (d, J=7.6 Hz, 1H) 4.76 (dd, J=5.1 Hz, J'=2.6 Hz, 1H) 4.29-4.20 (m, 3H) 4.01 (d, J=6.8 Hz, 1H) 3.75 (d, J=15.8 Hz, 1H) 3.60 (exch. d, J=5.1 Hz, 1H) 3.39 (br d, 1H) 2.60 (m, 1H) 2.34 (s, 3H) 2.34-2.22 (m, 2H) 1.90-1.71 (m, 2H) 1.62 (s, 3H) 1.61 (s, 3H) 1.53 (exch. d, J=7.8 Hz, 1H) 1.14 (s, 3H) 1.12 (s, 3H).

High Res. Mass Spectrum: Calcd for $C_{45}H_{50}NO_{12}$ (MH+) 796.3333, found 796.3319.

EXAMPLE 11

2'-O-benzyloxycarbonyl-7-epi-10-deacetyl taxol (11)

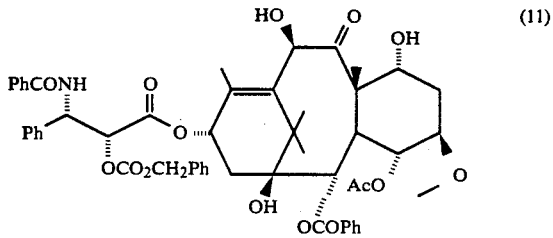

10-Deacetyl-7-epitaxol [see Samaranayake, G. et al "Modified Taxols. 5 . . . ," *J. Org. Chem.*, 1991, 56:5114-5119] (102 mg, 0.126 mmol) in dry dichloromethane (3 mL) was treated with diisopropylethylamine (0.0662 mL, 0.378 mmol) and benzyl chloroformate (0.0358 mL, 0.252 mmol) at room temperature. After overnight stirring, work-up and chromatography (60% ethyl acetate in hexane) gave 11 as a colorless oil (97 mg, 81%). NMR (300 MHz, CDCl3)δ 8.15 (d, J=8.5 Hz, 2H) 7.69 (d, J=8.5 Hz, 2H) 7.59-7.20 (m, 16H) 6.96 (exch. d, J=9.4 Hz, 1H) 6.26 (br t, 1H) 5.99 (dd, J=9.4 Hz, J'=2.7 Hz, 1H) 5.72 (d, J=7.4 Hz, 1H) 5.46 (d, J=2.7 Hz, 1H), 5.43 (s, 1H) 5.15 (AB q, 2H) 4.90 (m, 1H) 4.73 (d, J=11.8 Hz, 1H) 4.42 (AB q, 2H) 4.08 (s, 1H) 3.91 (d, J=7.4 Hz, 1H) 3.65 (br d, 1H) 2.52 (s, 3H) 2.41-2.00 (m, 5H) 1.84 (s, 3H) 1.70 (s, 3H) 1.17 (s, 3H) 1.06 (s, 3H).

High Res. Mass Spectrum: Calcd for $C_{53}H_{56}NO_{15}$ (MH+) 946.3650, found 946.3638.

EXAMPLE 12

2'-O-benzyloxycarbonyl-10-desacetoxy-11,12-dihydrotaxol-10,12(18)-diene (12)

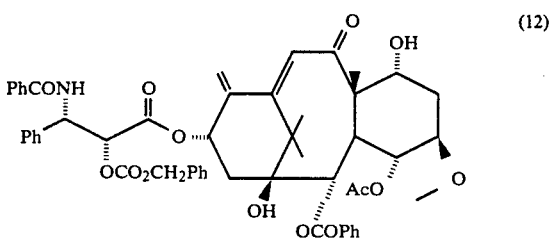

Carbonate 11 (97 mg, 0.103 mmol) in dry dichloromethane (3 mL) was treated with TFCT (0.050 mL, 0.308 mmol) at room temperature. After 15 h, the solution was concentrated and the residue chromatographed on silica gel (40% ethyl acetate in hexane) to afford 12 (37 mg, 39%) as a foam. Also recovered was unreacted starting material (39 mg, 40%). Compound 12 had NMR (300 MHz, CDCl3)δ 8.21 (d, J=8.5 Hz, 2H) 7.68 (d, J=8.4 Hz, 2H) 7.65-7.25 (m, 16H) 6.91 (exch.d, J=9.6 Hz, 1H) 6.24 (br t, 1H) 6.04 (s, 1H) 5.96 (dd, J=9.6 Hz, J'=2.2 Hz, 1H) 5.80 (d, J=8.0 Hz, 1H) 5.45 (d, J=2.2 Hz, 1H) 5.36 (d, J=2.3 Hz, 1H) 5.17 (AB q, 2H) 4.98 (d, J=2.3 Hz, 1H) 4.92 (br t, 1H) 4.71 (exch.d, J=11.9 Hz, 1H) 4.38 (AB q, 2H) 3.87 (m, 1H) 3.71 (d, J=8.0 Hz, 1H) 2.53 (s, 3H) 2.35 (m, 2H) 2.14 (m, 2H) 1.79 (s, 1H) 1.73 (s, 3H) 1.14 (s, 3H) 1.07 (s, 3H).

High Res. Mass Spectrum: Calcd for $C_{53}H_{54}NO_{14}$ (MH+) 928.3544, found 928.3542.

EXAMPLE 13

7-Epi-10-desacetoxytaxol (13)

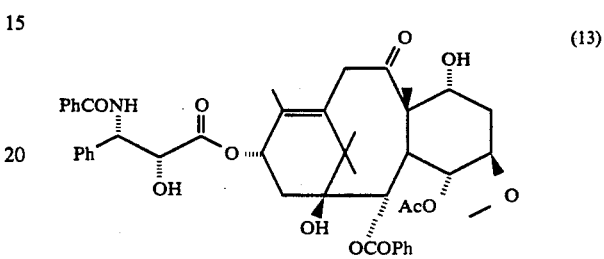

Dienone 12 (37 mg, 0.040 mmol) in ethyl acetate (1 mL) was treated with palladium on charcoal (12.7 mg, 10%, 0.012 mmol) and the slurry stirred under a hydrogen atmosphere for 12 h. The mixture was filtered and the filtrate concentrated. Silica gel chromatography (40% ethyl acetate in hexane) gave 18.6 mg (58%) of 13 as a foam. NMR (300 MHz, CDCl3)δ 8.17 (d, J=8.5 Hz, 2H) 7.72 (d, J=8.4 Hz, 2H) 7.68-7.29 (m, 11H) 6.98 (exch. d, J=9.0 Hz, 1H) 6.14 (br t, 1H) 5.81-5.73 (m, 2H) 4.89 (m, 1H) 4.76 (dd, J=5.2 Hz, J'=2.7 Hz, 1H) 4.57 (exch. d, J=11.9 Hz, 1H) 4.38 (s, 2H) 4.17 (d, J=7.3 Hz, 1H) 4.07 (d, J=16.6 Hz, 1H) 3.76 (m, 1H) 3.45-3.29 (m, 2H) 2.50 (s, 3H) 2.48-2.22 (m, 4H) 1.72 (s, 1H) 1.69 (s, 3H) 1.63 (s, 3H) 1.14 (s, 3H) 1.06 (s, 3H).

High Res. Mass Spectrum: Calcd for $C_{45}H_{50}NO_{12}$ (MH+) 796.3333, found 796.3309.

EXAMPLE 14

2'-O-allyloxycarbonyl-10-deacetyl-7-epitaxol (14)

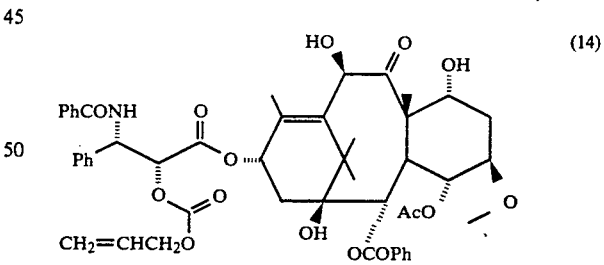

10-deacetyl-7-epitaxol (74 mg, 0.091 mmol) in dry dichloromethane (2 mL) was treated with pyridine (0.022 mL, 0.274 mmol) and allyl chloroformate (0.030 mL, 0.274 mL). The reaction mixture was stirred overnight at room temperature. Work-up and chromatography (60% ethyl acetate in hexane) afforded 14 as a foam (64 mg, 90%). NMR (300 MHz, CDCl3)δ 8.15 (d, J=8.5 Hz, 2H) 7.71 (d, J=8.4 Hz, 2H) 7.68-7.30 (m, 11H) 6.95 (exch. d, J=9.4 Hz, 1H) 6.26 (br t, 1H) 5.99 (dd, J=9.4 Hz, J'=2.7 Hz, 1H) 5.83 (m, 1H) 5.71 (d, J=7.4 Hz, 1H) 5.44-5.24 (m, H) 4.90 (m, 1H) 4.73 (exc. d, J=11.9 Hz, 1H) 4.62 (m, 2H) 4.41 (br s, 2H) 4.09 (exch. s, 1H) 3.90 (d, J=7.4 Hz, 1H) 3.65 (m, 1H) 2.54 (s, 3H) 2.43-1.98

(m, 4H) 1.89 (s, 3H) 1.80 (s, 1H) 1.78 (s, 3H) 1.16 (s, 3H) 1.06 (s, 3H).

High Res. Mass Spectrum: Calcd for $C_{49}H_{54}NO_{15}$ $(MH^+)$ 896.3493, found 896.3459.

EXAMPLE 15

2'-O-allyloxycarbonyl-10-desacetoxy-11,12-dihydro-7-epitaxol-10,12(18)-diene (15)

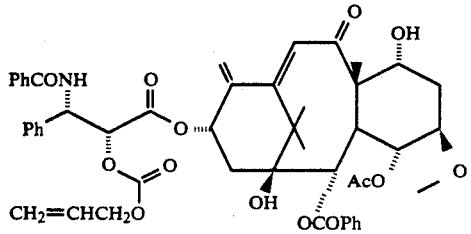

Carbonate 14 (73.9 mg, 0.083 mmol) in dry dichloromethane (2 mL) was treated with TFCT (0.040 mL, 0.248 mmol) and the resulting solution stirred at room temperature overnight. The solvent was evaporated and the residue chromatographed (silica gel, 40% ethyl acetate in hexane) to afford 15 as a white foam (30 mg, 41%), along with some unreacted starting material (17 mg, 19%). Compound 15 had NMR (300 MHz, $CDCl_3$)δ 8.19 (d, J=8.5 Hz, 2H) 7.68 (d, J=8.4 Hz, 2H) 7.68–7.22 (m, 11H) 6.95 (exch. d, J=9.7 Hz, 1H) 6.23 (br t, 1H) 6.02 (s, 1H) 5.97 (dd, J=9.7 Hz, J'=2.1 Hz, 1H) 5.86 (m, 1H) 5.78 (d, J=8.1 Hz, 1H) 5.42–5.23 (m, 4H) 4.97 (d, J=1.9 Hz, 1H) 4.94 (br t, 1H) 4.71 (exch. d, J=11.9 Hz, 1H) 4.62 (m, 2H) 4.38 (AB q, 2H) 3.83 (m, 1H) 3.69 (d, J=8.1 Hz, 1H) 2.52 (s, 3H) 2.50–1.80 (m, 5H) 1.76 (s, 3H) 1.12 (s, 3H) 1.05 (s, 3H).

High Res. Mass Spectrum: Calcd for $C_{49}H_{52}NO_{14}$ $(MH^+)$ 878.3388, found 878.3411.

EXAMPLE 16

10-Desacetoxy-11,12-dihydro-7-epitaxol-10,12(18)-diene (16)

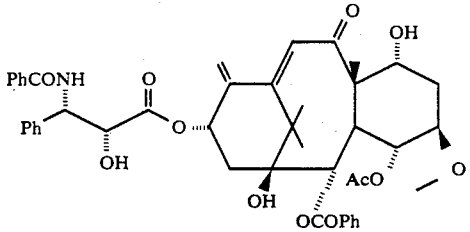

Dienone 15 (35 mg, 0.040 mmol) in dry THF (1 mL) was treated with a dichloromethane solution of tetrakis(triphenylphosphine)palladium (0.040M, 0.01 mL). Acetic acid (0.011 mL, 0.200 mmol) was added, followed by tributyltin hydride (0.0216 mL, 0.080 mmol). The reaction mixture was stirred at room temperature for 30 min, evaporated, and the residue was dissolved in acetonitrile (5 mL), washed with hexanes (3 portions of 1.5 mL). The acetonitrile layer was concentrated and the residue chromatographed (silica gel, 50% ethyl acetate in hexane) to afford 16 (13 mg, 40%) as a foam. Compound 16 can also be hydrogenated to yield the previously prepared 10-desoxy derivative 13. Compound 16 had NMR (300 MHz, $CDCl_3$)δ 8.22 (d, J=8.5 Hz, 2H) 7.64 (d, J=8.4 Hz, 2H) 7.63–7.25 (m, 11H) 6.93 (exch. d, J=9.5 Hz, 1H) 6.23 (br t, 1H) 6.01 (s, 1H) 5.78 (m, 2H) 5.28 (d, J=1.9 Hz, 1H) 4.93 (br t, 1H) 4.80 (d, J=1.9 Hz, 1H) 4.75 (dd, J=4.0 Hz, J'=2.1 Hz, 1H) 4.71 (exch. d, J=11.9 Hz, 1H) 4.37 (AB q, 2H) 3.83 (m, 1H) 3.69 (d, J=7.9 Hz, 1H) 3.35 (exch. d, J=4.0 Hz, 1H) 2.53 (s, 3H) 2.34–2.02 (m, 4H) 1.80 (s, 1H) 1.72 (s, 3H) 1.13 (s, 3H) 1.05 (s, 3H).

High Res. Mass Spectrum: Calcd for $C_{45}H_{47}N_{12}K$ $(MK^+)$ 832.2735, found 832.2754.

We claim:
1. A compound of the formula

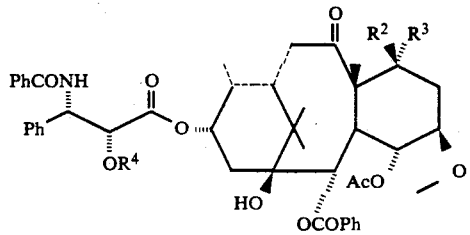

wherein
$R^2$ is hydrogen and $R^3$ is hydroxy; or $R^3$ is hydrogen and $R^2$ is hydroxy, chlorofluoroacetoxy, or a protected hydroxy group;

$R^4$ is hydrogen or a hydroxy protecting group; and the dash bonds together represent 10,12-diene or 11-ene; with the proviso that when $R^3$ is hydroxy and $R^2$ is hydrogen, or when $R^3$ is hydrogen and $R^2$ is hydroxy or a protected hydroxy group, the dash bonds together represent 10,12-diene.

2. A compound of claim 1 wherein $R^2$ is chlorofluoroacetoxy and $R^3$ is hydrogen.

3. A compound of claim 2 wherein the dash bonds together represent 11-ene.

4. A compound of claim 2 wherein the dash bonds together represent 10,12-diene.

5. A compound selected from the group consisting of 2'-O-allyloxycarbonyl-7-O-chlorofluoroacetyl-10-desacetoxy-11,12-dihydrotaxol-10,12(18)-diene; 7-O-chlorofluoroacetyl-10-desacetoxy-11,12(18)-dihydrotaxol-10,12(18)-diene; 7-O-chlorofluoroacetyl-10-desacetoxytaxol; and 2'-O-benzyloxycarbonyl-7-chlorofluoroacetyl-10-desacetoxy-11,12-dihydrotaxol-10,12(18)-diene.

6. A compound of claim 1 wherein the dash bonds together represent 10,12-diene.

7. A compound selected from the group consisting of 2',7-bis-O-(2,2,2-trichloroethoxycarbonyl)-10-desacetoxy-11,12-dihydrotaxol-10,12(18)-diene; 10-desacetoxy-11,12-dihydrotaxol-10,12(18)-diene; 2'-O-benzyloxycarbonyl-10-desacetoxy-11,12-dihydrotaxol-10,12(18)-diene; 2'-O-allyloxycarbonyl-10-desacetoxy-11,12-dihydro-7-epitaxol-10,12(18)-diene; and 10-desacetoxy-11,12-dihydro-7-epitaxol-10,12(18)-diene.

* * * * *